United States Patent [19]

Kitagawa et al.

[11] Patent Number: 4,677,213

[45] Date of Patent: Jun. 30, 1987

[54] 2,5-DIAMINO-1,4-DIOXANE DERIVATIVES AND PROCESS FOR PRODUCTION THEREOF

[75] Inventors: Sadao Kitagawa; Takashi Yokoi; Mitsumasa Kaito, all of Ami, Japan

[73] Assignee: Research Association for Utilization of Light Oil, Tokyo, Japan

[21] Appl. No.: 671,551

[22] Filed: Nov. 14, 1984

[30] Foreign Application Priority Data

Nov. 22, 1983 [JP] Japan .................. 58-220146

[51] Int. Cl.$^4$ .......................................... C07D 319/12
[52] U.S. Cl. .................................. 549/377; 549/378; 549/380
[58] Field of Search ................. 549/377, 378, 380

[56] References Cited

FOREIGN PATENT DOCUMENTS 292973  7/1971  U.S.S.R. ........................... 549/377

OTHER PUBLICATIONS

Chemical Abstract, 95:115411p (Kunetsov), (1981) previously cited.
Chemical Abstract, 65:15481a (1966).
Chemical Abstract, 56:3476i–3477a (1962).
J. Amer. Chem. Soc., 75, 4337 (1953).
Baum, Journ. Amer. Chem. Soc., 90 (25), Dec. '68, pp. 7083–7089.
Grimmett et al., Aust. J. Chem., 18, 1855 (1965).
Kuznetsov et al., Ukr. Khim. Za., 47, 746 (1981).
Laufer et al., Z. Anal Chem., 181, 494–503 (1961).
Heyns et al., Carbohydrate Res., 2, 328–337 (1966).
Carson, Jacs, 75, 4337 (1953).

*Primary Examiner*—Nicky Chan
*Attorney, Agent, or Firm*—Robert E. Burns; Emmanuel J. Lobato; Bruce L. Adams

[57] ABSTRACT

Dioxane derivatives are disclosed which are represented by the formula (I):

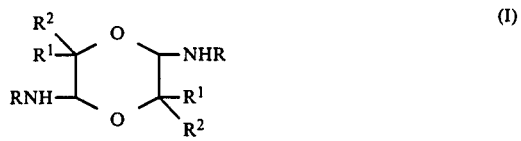

wherein, R stands for a hydrogen atom or an aliphatic residue having 1 to 10 carbon atoms; $R^1$ and $R^2$ stand for a hydrogen atom or a hydrocarbon residue having 1 to 10 carbon atoms, respectively; and R, $R^1$ and $R^2$ which exist plurally may be the same or different, respectively.

Such dioxane derivatives (I) are produced by reacting a glycolaldehyde represented by the formula (II)

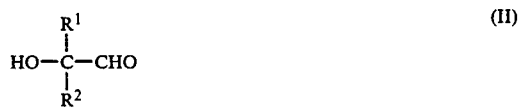

with an amine represented by the formula (III)

R—NH$_2$ (III)

wherein R, $R^1$ and $R^2$ are as defined above.

The dioxane derivatives (I) are useful for production of serine derivatives as well as utilized for separation and purification of glycolaldehydes (II).

2 Claims, 2 Drawing Figures

2,5-DIAMINO-1,4-DIOXANE DERIVATIVES AND PROCESS FOR PRODUCTION THEREOF

BACKGROUND OF THE INVENTION

This invention relates to dioxane derivatives and a process for production thereof.

Dioxane derivatives which have unsubstituted amino groups or mono-substituted amino groups on the 2- and 5-positions of a 1,4-dioxane are novel and not known in the art. Such dioxane derivatives, if available, might be expected to be useful as the intermediates of medical drugs, agricultural chemicals, etc. as well as the additives for thermoplastic and thermosetting resins or the intermediates thereof, but have not been actually used because they were not available.

SUMMARY OF THE INVENTION

The present invention is based on the findings that such dioxane derivative compounds can be synthesized.

The dioxane derivatives of the present invention are represented by the following formula (I).

The process for production of the dioxane derivatives according to the present invention is characterized by reacting a glycolaldehyde represented by the following formula (II) with an amine represented by the following formula (III):

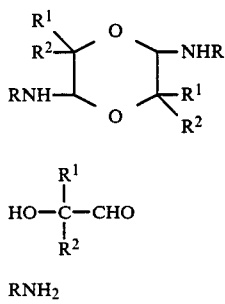

$$\text{HO}-\underset{\underset{R^2}{|}}{\overset{\overset{R^1}{|}}{C}}-\text{CHO} \quad (II)$$

$$RNH_2 \quad (III)$$

wherein, R stands for a hydrogen atom or an aliphatic residue having 1 to 10 carbon atoms, each of $R^1$ and $R^2$ stands for a hydrogen atom or a hydrocarbon residue having 1 to 10 carbon atoms, and R, $R^1$ and $R^2$ which exist plurally may be the same or different, respectively.

DETAILED DESCRIPTION OF THE INVENTION

Figure 1:
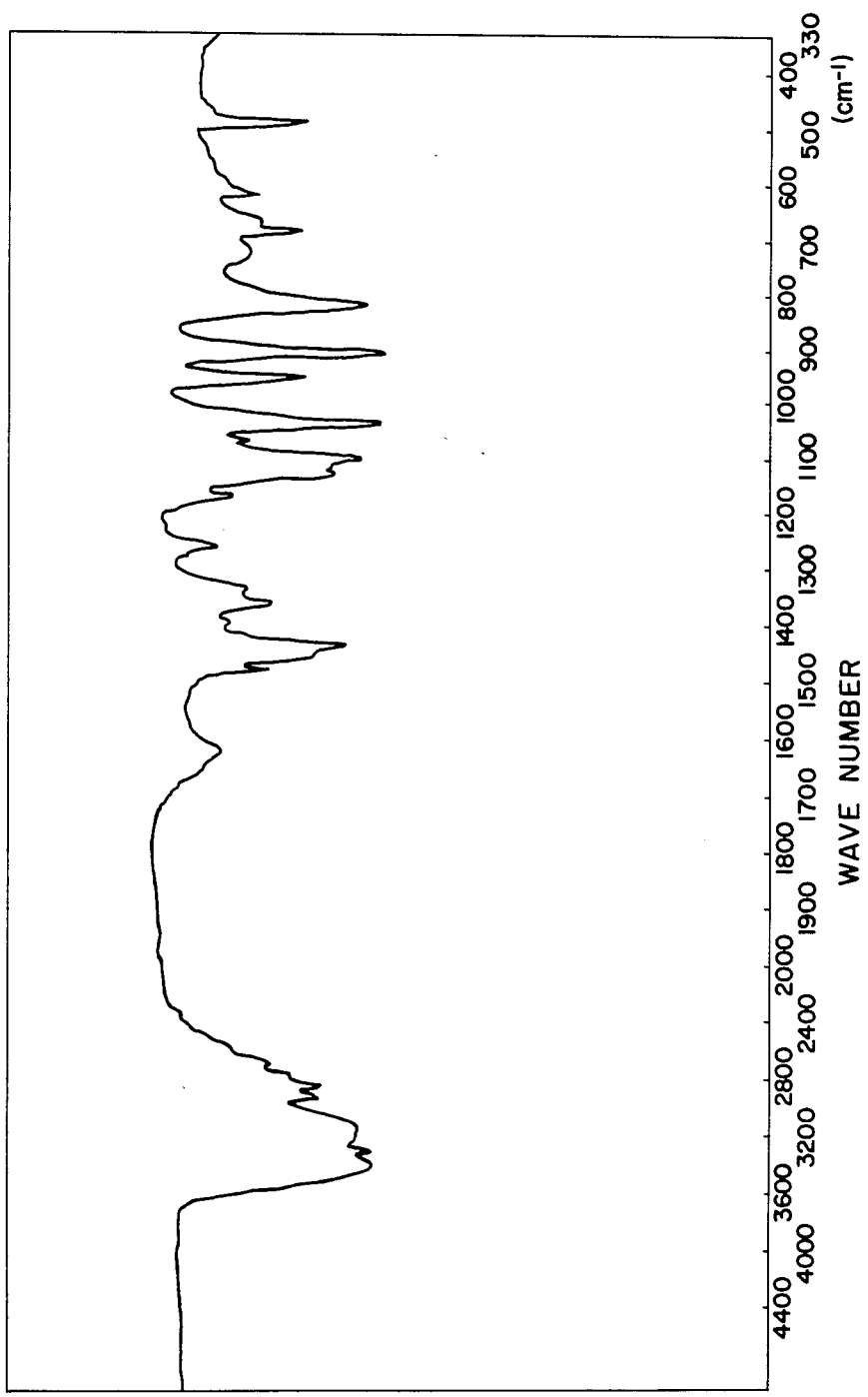
FIGS. 1 and 2 show an infrared absorption spectrum and a nuclear magnetic resonance spectrum ($^1H$, $D_2O$, 270MH$_z$) of 2,5-diamino-1,4-dioxane obtained in Example 1 herein, respectively. The symbol A in FIG. 2 shows the spectrum of an internal standard ($CH_3Si(CH_2)_3SO_3Na$).

Analysis of the Present Invention in the Light of Prior Art

It has been presumed that a dioxane derivative wherein R in the formula (I) corresponds to an aromatic residue is contained in the reaction mixture obtained by mixing a glycolaldehyde with an aromatic primary amine in water, by means of infrared absorption spectra thereof (Z. für analytische Chemie 181, 494(1961)).

On the other hand, it is known that a small quantity of glyoxal-dicyclohexylimine is obtained by reacting a glycolaldehyde with cyclohexylamine in the presence of air. In this reaction, however, there has not been obtained a dioxane derivative wherein R in the formula (I) corresponds to cyclohexyl group (J. Am. Chem. Soc. 75, 4337(1953)).

In the former prior process mentioned above, it is considered that 2,5-bis(phenylamino)-1,4-dioxane is formed via an intermediate, glycolaldehyde-N-phenylimine.

Generally in a reaction of an aldehyde with an amine to produce an imine, it is well known that the imine is produced in a high yield when an aromatic amine is used as the amine, but when ammonia or an aliphatic amine is used most of the resulting imine can not be stably isolated.

According to the results of the latter prior process mentioned above, it has been believed by those skilled in the art that the dioxane derivative of the present invention can not be obtained by reacting a glycolaldehyde with ammonia or an aliphatic amine.

Thus, it is indeed a surprising fact that the present dioxane derivative can be readily obtained from a glycolaldehyde and ammonia or an aliphatic amine. This process is one of the typical processes according to the present invention.

Dioxane Derivatives

The dioxane derivative of the present invention is represented by the aforementioned formula (I).

In the formula (I), R is hydrogen atom or an aliphatic residue having 1 to 10 carbon atoms, preferably hydrogen atom or an aliphatic residue having 1 to 5 carbon atoms, most preferably hydrogen atom. When R is an aliphatic residue, it is typically a hydrocarbon residue. The aliphatic hydrocarbon residue may have a halogen, hydroxyl group, carboxyl group, carbamoyl group, an alkoxycarbonyl group, and the like bonded thereto. Thus, the R is referred to herein as "aliphatic residue", not as "aliphatic hydrocarbon residue."

In the formula (I), $R^1$ and $R^2$ are hydrogen atom or an aliphatic or aromatic hydrocarbon residue having 1 to 10 carbon atoms, preferably hydrogen atom or a hydrocarbon residue (especially aliphatic) having 1 to 6 carbon atoms, most preferably hydrogen atom, respectively. It is preferred that R, $R^1$ and $R^2$, which exist plurally, are the same, respectively.

Synthesis of Dioxane Derivatives

There are a variety of processes for producing the present dioxane derivatives, which are exemplified by (a) a reaction of a glycolaldehyde (Formula (II)) with ammonia or an aliphatic primary amine (Formula (III)) corresponding to the above mentioned R, (b) a reaction of a 2,5-dihalo-1,4-dioxane with ammonia or the above mentioned primary amine, (c) Hofmann degradation of 2,5-dicarbamoyl-1,4-dioxane, etc. An especially preferable process is that of the reaction of a glycolaldehyde (II) with ammonia or an aliphatic primary amine (III). Incidentally, the preferable R, $R^1$ and $R^2$ groups in the formulas (II) and (III) are as described above.

The reaction of a glycolaldehyde with ammonia or an aliphatic primary amine to produce the present dioxane derivative can be conducted in the presence or absence of a solvent. The reaction is preferably carried out under such conditions as to substantially prevent the glycolaldehyde from oxidation. It is thus preferred that the reaction is carried out under a stream of an inert gas such as nitrogen or argon or in a sealed system. In the latter case, possible presence of a small quantity of oxygen in the sealed system is allowable. The reaction temperature is generally in the range of −10° to 100° C., preferably 0° to 70° C., especially 10° to 50° C. The reaction time is approximately in the range of generally 1 minute to 5 days, preferably 1 hour to 1 day. The quantity of ammonia or the aliphatic primary amine is generally 0.5 mol or more, preferably 1 mol or more per mol of the glycolaldehyde. The upper limit of the quantity to be used is not especially restricted, and an optional quantity of 0.5 mol or more can be used as far as economically allowable. Incidentally, in the above mentioned reaction, the dioxane derivative can be produced by simply mixing the raw or starting materials or in the presence of a catalyst such as an acid, an alkali, etc.

Utility of the Dioxane Derivatives

The present dioxane derivatives are useful as the intermediates of medical drugs, agricultural chemicals, α-amino acids, etc. as well as the additives for thermosetting or thermoplastic resins, rubbers (natural and synthetic) and the like or the intermediates of such additives.

More particularly, as an example of specific uses of the present dioxane derivatives, a serine derivative can be produced from the dioxane derivative and hydrocyanic acid.

The serine derivative produced from the present dioxane derivative and hydroxyanic acid is obtained in the form of a DL-compound as usually obtained by chemical synthesis. The serine derivatives produced according to the present invention include DL-serine compound as well as DL-serine derivatives wherein hydrogen of N- and/or methylene group of the serine has been substituted.

The DL-serine derivatives, which have or have not undergone optical resolution, are useful as physiologically active substances such as medical drugs or raw or starting materials therefor, cosmetics or raw or starting materials therefor, or the raw or starting materials for α-amino acids such as tryptophan, cysteine and cystine.

Also, the present invention can be utilized as a means for separation and purification of glycolaldehydes, which comprises reacting an amine represented by the aforementioned formula (III) with a solution having a glycolaldehyde, represented by the aforementioned formula (II) to form a dioxane derivative (I) of the present invention, recovering the dioxane derivative, and then decomposing the dioxane derivative in contact with an acid to obtain the corresponding purer glycolaldehyde.

The glycolaldehydes are useful as the synthetic intermediates of various chemicals such as amino acids, because they have both alcoholic hydroxyl group and formyl group. The glycolaldehydes may be produced by an oxidation reaction process of ethylene glycols, a reaction process of the so-called $C_1$ chemistry comprising reaction of formaldehyde, carbon monoxide and hydrogen, etc. Although the synthetic process itself is relatively easy, the glycolaldehydes have not been produced in an industrial scale because separation and purification of the resulting reaction mixtures are difficult. Thus, the method for separation and purification of glycolaldehydes according to the present invention is considered to be useful.

Experiments

EXAMPLE 1

A 20 ml flask replaced with nitrogen was charged with 2.4 g of glycolaldehyde and 5.3 ml of 25% aqueous ammonia. The mixture was sealed and subjected to reaction at 25° C. for 4 hours. White crystals separated out was filtered and dried to give 1.56 g of the crystals. The filtrate was concentrated to further obtain 0.64 g of white crystals. The total yield was 93% on the basis of glycolaldehyde.

As a result of differential thermal analysis (decomposed at 130° C.), elemental analysis, infrared absorption spectrum and nuclear magnetic resonance spectrum ($^1H$, $D_2O$ solvent), the white crystal was identified to be 2,5-diamino-1,4-dioxane.

| (a) Elemental analysis: | C (%) | H (%) | N (%) |
|---|---|---|---|
| Calculated (as $C_4H_{10}N_2O_2$) | 40.67 | 8.53 | 23.7 |
| Found | 40.17 | 8.10 | 23.2 |

Figure 2:
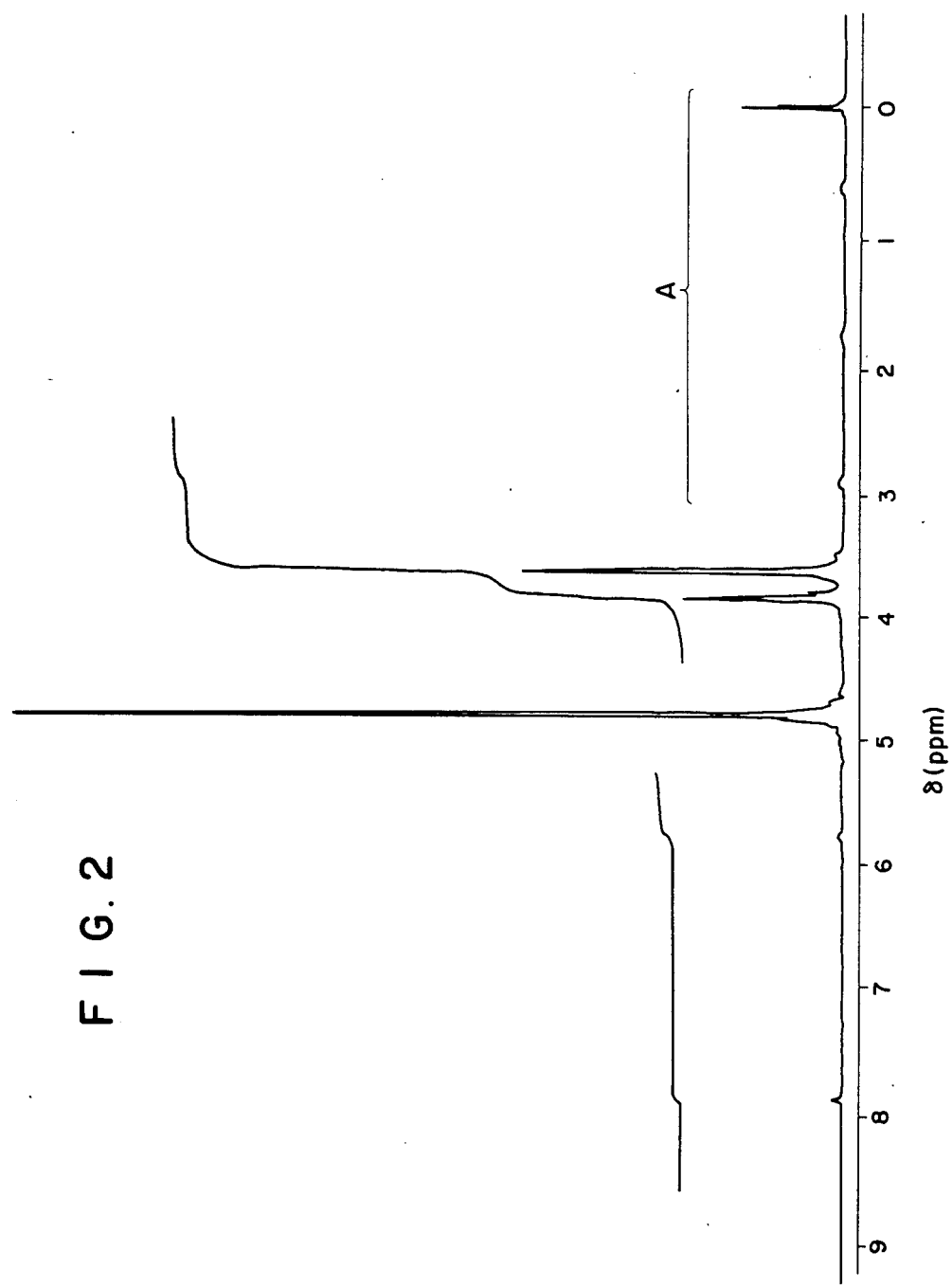

(b) The infrared absorption spectrum is shown in FIG. 1, and the nuclear magnetic resonance spectrum in FIG. 2, respectively.

Incidentally, 2,5-diamino-1,4-dioxane thus obtained was analyzed by high performance liquid chromatography, and its purity was 99.2%.

EXAMPLE 2

0.6 g of glycolaldehyde and 1.2 g of an aqueous solution containing 40% monomethyl amine were subjected to reaction under the same conditions as in Example 1. The resulting reaction mixture was concentrated to obtain 0.63 g of viscous 2,5-dimethylamino-1,4-dioxane (yield 92% on the basis of glycolaldehyde).

| Elemental analysis: | C (%) | H (%) | N (%) |
|---|---|---|---|
| Calculated (as $C_6H_{14}N_2O_2$) | 49.30 | 9.65 | 19.16 |
| Found | 49.01 | 9.14 | 18.09 |

EXAMPLE 3

A 300 ml autoclave was charged with a solution of 8.8 g glycolaldhyde dissolved in 52.2 g of a 85/15 (by weight) mixture of ethylene glycol and water and then 30 ml of liquid ammonia. The mixture was subjected to reaction at 20° C. for 5 hours. After the reaction, ammonia was purged and white solid separated out was filtered. The filtered solid was washed with ether and then vacuum-dried to obtain 8.1 g of 2,5-diamino-1,4-dioxane. The yield corresponds to 93.2% on the basis of glycolaldehyde.

EXAMPLE 4

A mixture of 0.9 g of glycolaldehyde, 1.0 g of n-hexylamine and 5.0 ml of water was agitated in a sealed vessel at 50° C. for 7 hours. The reaction mixture obtained was subjected to extraction with chloroform, the extract was dried over anhydrous sodium sulfate, and the chloroform was evaporated off to produce, as a viscous liquid material, 0.61 g of 2,5-di-n-hexylamino-1,4-dioxane. The yield was 43% based on the n-hexylamine.

| Elemental analysis: | C (%) | H (%) | N (%) |
|---|---|---|---|
| Calculated (as $C_{16}H_{34}N_2O_2$) | 67.09 | 11.96 | 9.78 |
| Found | 67.25 | 11.23 | 9.17 |

EXAMPLE 5

Example 4 was repeated except for the use of 0.9 g of β-alanineamide instead of n-hexylamine to produce, as a paste material, 0.48 g of 2,5-bis(β-carbamoylethylamino) 1,4-dioxane. The yield was 37% based on the β-alanineamide.

| Elemental analysis: | C (%) | H (%) | N (%) |
|---|---|---|---|
| Calculated (as $C_{10}H_{20}N_4O_4$) | 46.14 | 7.74 | 21.52 |
| Found | 45.98 | 7.61 | 22.81 |

The present invention is further described on the processes for production of serine derivatives in which the present dioxane derivatives (I) is utilized.

Reaction: the first step

This step is essentially related to the reaction of a dioxane derivative with hydrocyanic acid.

A solvent is normally used in the reaction. The solvents include, for example, water, an alcohol such as methanol or ethanol, etc. Especially, water is preferably used. The reaction temperature is approximately in the range of generally −10° to 100° C., preferably 0° to 80° C., especially 10° to 50° C. The reaction time is generally 10 minutes or more and preferably 30 minutes or more. The upper limit of the reaction time is not especially restricted. In general, the reaction up to 24 hours is enough, and most reactions are terminated in about 5 hours. The molar ratio of the dioxane derivative to hydrocyanic acid (the amount thereof to be added or a theoretical amount when hydrocyanic acid is generated in situ in the reaction system from a cyanide and an organic or inorganic acid, an inorganic salt or the like) is approximately in the range of generally from 1.0 to 10 mols, preferably from 1.6 to 5 mols of hydrocyanic acid per mol of the dioxane derivative.

It is not confirmed yet what compound is formed by the reaction of the dioxane derivative with hydrocyanic acid. According to an assumption, however, the resulting compound is considered to be a precursor with respect to the carboxyl group of a serine derivative desired and to be $HOCH_2CH(NH_2)CN$ in the case of serine. The present invention, however, is not to be bound by such assumption.

Reaction: the second step

This step is essentially related to formation of a serine derivative by subjecting a reaction product of the first step (i.e. the above mentioned intermediate compound which was isolated or not isolated) to an aqueous alkaline or acidic condition.

The aqueous alkaline or acidic condition is a condition which causes hydrolysis. When the intermediate compound from the first step is a nitrile, the cyano group is hydrolyzed into carboxyl group to form the corresponding serine derivative.

Irrespective of the type of the intermediate compound from the first step, "the aqueous alkaline or acidic condition" can be the conventional condition which is usually used in the hydrolysis of organic nitrile compounds or hydantoin compounds with an alkali or an acid.

Isolation of the resulting serine derivative

In the reaction product of the second step, the DL-serine derivative is usually present in the form of a salt, from which a free DL-serine derivative can be isolated by a conventional method. Such conventional methods for isolation include, for example, a method of neutralizing the reaction mixture with an acid or an alkali to an isoelectric point and then subjecting the neutralized mixture to fractional crystallization, a method of passing the reaction mixture through a cation- or anion-exchange resin and then subjecting it to elution.

The yield of DL-serine or an N-substituted-DL-serine in the experiments given below was obtained by the following high performance liquid chromatography.

Type: Shimazu LC-5A high performance liquid chromatograph
Column: Shimazu Shim-pack ISC-07/S1504
Detector: Shimazu SPD-2A type UV detector (195 nm)
Mobile phase: $0.1N-NaH_2PO_4/0.25\%H_3PO_4$ aqueous solution
Temperature: 55° C.
Pressure: 45 Kg/cm$^2$
Flow rate: 5 ml/minute

REFERENCE EXAMPLE 1

To 10 ml of water were added 1.18 g (10 m mol) of 2,5-diamino-1,4-dioxane, 0.98 g (20 m mol) of sodium cyanide and 2.15 g (40 m mol) of ammonium chloride. The mixture was subjected to reaction at 25° C. for 3 hours. To this reaction mixture was added 35 ml of an aqueous solution containing 4.0 g (100 m mol) sodium hydroxide. The resulting mixture was subjected to hydrolysis reaction under reflux for 2 hours. A small quantity of the reaction mixture was taken out and vaporized to dryness, which was found to contain a large amount of sodium salt of DL-serine by means of infrared absorption spectrum. The yield of DL-serine was determined by high performance liquid chromatography to be 81%.

REFERENCE EXAMPLE 2

Reference Example 1 was repeated wherein the ammonium chloride was replaced with 2.64 g (20 m mol) of ammonium sulfate. The yield of DL-serine was 81%.

REFERENCE EXAMPLE 3

Reference Example 1 was repeated under the same conditions except that the hydrolysis reaction was carried out for 3 hours with 15 ml of 35% hydrochloric acid. The yield of DL-serine was 87%.

REFERENCE EXAMPLE 4

To 30 ml of an aqueous solution containing 1.18 g (10 m mol) 2,5-diamino-1,4-dioxane and 4.81 g (50 m mol) ammonium carbonate, was added dropwise 10 ml of an aqueous solution containing 0.55 g (20 m mol) hydrocyanic acid over 30 minutes, while the reaction mixture was kept at 25° C. After termination of the dropwise addition, the reaction was further continued at 25° C. for 4 hours. The reaction mixture was then transferred to a 100 ml stainless steel pressure-proof reaction tube, followed by addition thereto of 4 g (100 m mol) of sodium hydroxide and sealing. The resulting mixture was subjected to hydrolysis with shaking at 180° C. for 3 hours. The yield of DL-serine was 42%.

REFERENCE EXAMPLE 5

Reference Example 1 was repeated by replacing the 2,5-diamino-1,4-dioxane with 1.46 g (10 m mol) of 2,5-bis(methylamino)-1,4-dioxane. The yield of the resulting N-methyl-DL-serine was 80%.

REFERENCE EXAMPLE 6

Reference Example 1 was repeated except that 2.7 g (10 m mol) of 2,5-bis(phenylamino)-1,4-dioxane was used instead of the 2,5-diamino-1,4-dioxane and that 20 ml of water was used instead of 10 ml. The yield of N-phenyl-DL-serine was 75%.

COMPARATIVE REFERENCE EXAMPLE 1

Reference Example 1 was repeated wherein the 2,5-diamino-1,4-dioxane was replaced by 1.20 g (20 m mol) of glycolaldehyde. The yield of DL-serine was only 47%.

COMPARATIVE REFERENCE EXAMPLE 2

Reference Example 1 was repeated under the same conditions except that the 2,5-diamino-1,4-dioxane was replaced with 1.20 g (20 m mol) of glycolaldehyde and that 1.5 ml of 25% aqueous ammonia (22 m mol as $NH_3$) was added to a mixture of sodium cyanide, ammonium chloride and glycolaldehyde. The yield of DL serine was only 61%.

Incidentally, in order to obtain 75% yield of DL-serine in this Comparative Reference Example, the reaction time as long as 25 hours was required in the reactions of the glycolaldehyde, sodium cyanide, ammonium chloride and ammonia.

Moreover, the present invention is further described on the separation and purification of a glycolaldehyde from a solution containing the glycolaldehyde.

The term "a solution containing a glycolaldehyde" means a solution "derived from oxidation of ethylene glycol" as well as a solution "derived from a reaction of formaldehyde, carbon monoxide and hydrogen." Thus, the solution containing a glycolaldehyde encompasses a reaction solution itself of glycolaldehyde synthesis by these reactions, as well as a glycolaldehyde solution obtained by purifying the process product from the synthesis at least partially, for example, a glycolaldehyde solution obtained by separating a solvent used from the process product (a portion of accompanying impurities may be separated at the same time) and redissolving the resulting crude glycolaldehyde in a suitable solvent. Examples of such solvents include water, ethylene glycol, methanol, ethanol, dimethylformamide, dimethyl sulfoxide, and mixtures thereof. Of these solvents, preferred are water, methanol, ethanol, ethylene glycol and dimethylformamide.

The concentration of a glycolaldehyde in the solvent can be suitably selected from the viewpoint of preparation and handling of the solution as well as the subsequent steps. Specifically, the concentration is approximately in the range of 2 to 70% by weight.

As to the method for separating a dioxane derivative from the reaction products containing the dioxane derivative (I) produced by the present process, a variety of methods can be employed which are fit for the properties of the dioxane derivative.

When the dioxane derivative is an easily crystallizable compound, the methods for separation include, for example, (1) a method of cooling the reaction mixture (e.g. to −10° to 30° C.); (2) a method of adding to the reaction mixture a precipitant which is a non-solvent to the dioxane derivative, such as benzene, toluene, diethyl ether, tetrahydrofuran, ethyleneglycol dimethyl ether, chloroform, methanol, ethanol, isopropyl alcohol, acetone, ethyl acetate, or dimethylformamide; (3) a method of concentrating the reaction mixture under normal or reduced pressure, especially under reduced pressure; or (4) combination of these methods; whereby crystals of the dioxane derivative can be formed and filtrated out (crystallization method).

When the dioxane derivative is a liquid product, the methods for separation include, for example, (5) a method of extracting and removing impurities with a solvent which does not dissolve the dioxane derivative substantially and can dissolve accompanying impurities, such as benzene, toluene, chloroform, diethyl ether, tetrahydrofuran, ethyleneglycol dimethyl ether, methanol, ethanol, isopropyl alcohol, acetone, ethyl acetate, and dimethylformamide; or (6) a method of concentration under normal or reduced pressure in combination with the above described method (5); whereby the dioxane derivative of high purity can be obtained.

Of the above mentioned methods, especially preferred is a crystallization method. Examples of the dioxane derivatives fit for the crystallization method include the dioxane derivative wherein the substituents $R^1$, $R^2$ and R are all hydrogen atoms. In most of these examples, crystals of the dioxane derivative are separated out by simply adding the corresponding amine to a solution containing glycolaldehyde at room temperature.

The dioxane derivative thus obtained is of high purity and contains substantially no impurities. Of course, the resulting dioxane derivative can be further purified by washing, recrystallization, etc. as necessary.

The dioxane derivative (I) thus recovered is contacted with an acid and decomposed to form glycolaldehyde (II).

The acid decomposition can be carried out by adding an acid to a solution or dispersion of the dioxane derivative and allowing the mixture to stand or stir at about 0° C. to about 100° C.

The acids to be used for the decomposition include (1) an inorganic acid such as hydrochloric acid, sulfuric acid and phosphoric acid, (2) an organic carboxylic acid such as formic acid, acetic acid, propionic acid and benzoic acid, (3) an organic sulfonic acid such as benzenesulfonic acid and toluenesulfonic acid, (4) a strongly acidic or weakly acidic ion-exchange resin, etc. As described above, the term "acid" herein means a liquid acid as well as a solid acid such as acidic ion-exchange resins. Such a solid acid is especially suitable when the dioxane derivative is treated in the form of a solution to obtain glycolaldehydes in high purity.

REFERENCE EXAMPLE 7 (PREPARATION OF THE COMPOUND (I))

Ammonia gas (53 m mol) was blown at room temperature into 10 g of a solution consisting (by weight) of 77.9% ethylene glycol, 13.9% glycolaldehyde, 0.9% glyoxal, 3.4% formic acid and 3.9% water, said solution having been obtained by oxidizing ethyleneglycol in a gaseous phase. The resulting mixture was sealed and stirred at room temperature for 4 hours. The reaction mixture containing a large amount of white crystals was allowed to stand overnight at 0° C. and then filtered. The filtered solid was washed with cooled isopropanol and then dried to obtain 1.29 g of 2,5-diamino-1,4-dioxane in white powder. This quantity of 2,5-diamino-1,4- dioxane corresponds to a recovering yield of 91.2% on the basis of glycolaldehyde. The 2,5-diamino-1,4-dioxane was subjected to high performance liquid chromatography analysis, and its purity was as high as 99.5% or more (single peak).

COMPARATIVE REFERENCE EXAMPLE 3

Ten (10) g of the gaseous oxidation reaction mixture of ethylene glycol used in Reference Example 7 was concentrated at 50° C. in a rotary evaporator to about 5 g and then allowed to stand overnight at 0° C. to give white solid product separated out. The solid product was filtered, washed with cooled isopropanol and dried to obtain 0.95 g of the product. As a result of high performance liquid chromatography analysis, the solid was found to be glycolaldehyde of 91.7% in purity. The recovering yield was as low as 60.5%.

REFERENCE EXAMPLE 8 (RECOVERY OF THE COMPOUND(I))

In 20 ml of water was dissolved 0.250 g of 2,5-diamino-1,4-dioxane obtained in Reference Example 7, followed by addition thereto of 10 ml (apparent volume) of a strongly acidic cation exchange resin ("Amberite IR-120" H type). The mixture was stirred at room temperature for 1 hour and then filtered to collect filtrate. The ion exchange resin was washed with water to collect a washing formed. A mixture consisting of the filtrate and the washing was subjected to high performance liquid chromatography analysis. The solution was found to contain 0.251 g of glycolaldehyde. No components other than glycolaldehyde were detected in this solution. Thus, it is clear that glycolaldehyde can be recovered quantitatively by the treatment of 2,5-diamino-1,4-dioxane with a strongly acidic cation exchange resin.

What is claimed is:

1. 2,5-Diamino-1,4-dioxane of the formula:

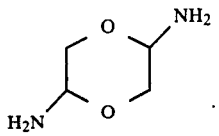

2. A process for the production of 2,5-diamino-1,4-dioxane of the formula,

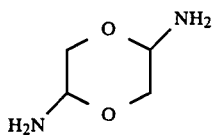

which comprises reacting glycolaldehyde of the formula, $HO-CH_2-CHO$, with ammonia of the formula, $-NH_3$, at a temperature of 0° to 70° C. under inert gas or in a sealed system to substantially prevent oxidation of glycolaldehyde and thereby produce 2,5-diamino-1,4-dioxane.

* * * * *